United States Patent [19]

Isacke et al.

[11] Patent Number: 5,051,364

[45] Date of Patent: Sep. 24, 1991

[54] ANTI-LIPOCORTIN-I AND ANTI-LIPOCORTIN-II MONOCLONAL ANTIBODIES

[75] Inventors: Clare M. Isacke, La Jolla; Ian S. Trowbridge; Tony Hunter, both of San Diego, all of Calif.

[73] Assignee: The Salk Institute for Biological Studies, San Diego, Calif.

[21] Appl. No.: 453,015

[22] Filed: Dec. 20, 1989

Related U.S. Application Data

[63] Continuation of Ser. No. 312,342, Feb. 16, 1989, abandoned, which is a continuation of Ser. No. 57,757, Jun. 3, 1987, abandoned.

[51] Int. Cl.$^5$ .................. C07K 15/28; C12N 5/12; A61K 39/00
[52] U.S. Cl. .................. 435/240.27; 530/387; 530/389; 424/85.8; 424/85.91; 435/70.21
[58] Field of Search ............... 530/387, 359, 808, 809; 435/70.21, 240.27, 240.2, 948; 424/85.8, 85.91; 436/548; 935/104.81, 107, 110

[56] References Cited

PUBLICATIONS

Glenney, J. "Two Related but Distinct Forms of the Mr 36,000 Tyrosine Kinase Substrate (Calpactin) that Interact with Phospholipid and Actin in a Ca$^{2+}$-Dependent Manner," *Proc. Nat'l. Acad. Sci.* 83:4258–4262, Jun. 1986.

Courtneidge, S. et al., "Subcellular Location of an Abundant Substrate (p. 36) for Tyrosine-Specific Protein Kinases," *Mol. Cell. Biol.* 3(3):340–350, Mar. 1983.

Goding, J. W., *Monoclonal Antibodies:Principles and Practice*, Academic Press, Inc., Orlando, 1983, pp. 68–70.

Morrison, S. L. "Transfectomas Provide Novel Chimeric Antibodies," *Science* 229:1202–1207, Sep. 20, 1985.

Sawyer, S. T. et al., "Epidermal Growth Factor Stimulates the Phosphorylation of the Calcium-Dependent 35,000-Dalton Substrate in Intact A-431 Cells," *J. Biol. Chem.* 260(14):8233–8236, Jul. 15, 1985.

Fava, R. et al., "Isolation of a Calcium-Dependent 35-Kilodalton Substrate for the Epidermal Growth Factor Receptor/Kinase from A-431 Cells," *J. Biol. Chem.* 259(4):2636–2645, Feb. 25, 1984.

*Primary Examiner*—Esther L. Kepplinger
*Assistant Examiner*—Paula Hutzell
*Attorney, Agent, or Firm*—Fitch, Even, Tabin & Flannery

[57] ABSTRACT

The present invention provides monoclonal antibodies which are specific for one but not both of human lipocortin-I and human lipocortin-II, as well as cultures of hybridomas and other types of cells producing such antibodies.

12 Claims, No Drawings

ANTI-LIPOCORTIN-I AND ANTI-LIPOCORTIN-II MONOCLONAL ANTIBODIES

The invention described and claimed herein is a result of work funded in part under grants from the United States National Institutes of Health. The United States Government has certain rights in said invention.

This application is a continuation of application Ser. No. 07/312,342 filed Feb. 16, 1989, abandoned, which is a continuation of application Ser. No. 07/057,757, filed June 3, 1987, abandoned.

TECHNICAL FIELD

This invention is directed to monoclonal antibodies and cultures of cells producing same. More particularly, the invention relates to such antibodies which recognize human lipocortin-I, also known as calpactin-II, or human lipocortin-II, also known as calpactin-I-heavy chain.

BACKGROUND OF THE INVENTION

Lipocortin-I is a known protein, of relative molecular weight of about 35 kilodaltons and conserved amino acid sequence, found in avian and mammalian species. The protein has been referred to by several names, in addition to lipocortin-I, including "p35," on account of its molecular weight, and "calpactin-II," due to its ability to bind calcium, phospholipid and acting, in a manner similar to calpactin-I, discussed below. In the present specification, the protein will be referred to as "lipocortin-I." The amino acid sequence of human lipocortin-I is provided in Wallner et al., Nature, 320, 77–81 (1986), and in Patent Cooperation Treaty Application Publication No. 86-04094, published July 17, 1986.

Lipocortin-I is a substrate for phosphorylation by protein kinase C and the protein-tyrosine kinase, epidermal growth factor receptor. Lipocortin-I is found in the same cell types as calpactin-I but, unlike calpactin-I-heavy chain, is potentially secreted from such cells, including macrophages in response to corticosteroids.

Lipocortin-I inhibits the enzyme phospholipase $A_2$. See Wallner et al., supra, and PCT Application Publication No. 86-04094.

Calpactin-I-heavy chain is a known protein, of relative molecular weight of about 36 kilodaltons and highly conserved amino acid sequence found in high concentration intracellularly in certain cells, especially epithelial and endothelial cells, of avian and mammalian species. The amino acid sequence of calpactin-I-heavy chain is highly homologous with that of lipocortin-I, and the two proteins have similar properties and functions.

Calpactin-I-heavy chain has been referred to by various names, including "p36," on account of its molecular weight, and "lipocortin-II" on account of the numerous properties it has in common with lipocortin-I, discussed above. In the present specification, calpactin-I-heavy chain will be referred to as "lipocortin-II." A partial amino acid sequence of human lipocortin-II is provided in PCT Application Publication No. 86-04094, wherein the protein is referred to as "N-lipocortin," and in Huang et al., Cell, 46, 191–199 (1986). The sequence of lipocortin-II (p36) is also provided in Saris et al., Cell, 46, 201–212 (1986), and reveals a multidomain protein with internal repeats.

Lipocortin-II is a substrate for phosphorylation by protein kinase C, retroviral protein-tyrosine kinases and other protein-tyrosine kinases, including epidermal growth factor receptor and platelet-derived growth factor receptor.

The protein, in association with the 11-kilodalton calpactin-I-light chain, forms calpactin-I, which binds calcium, phospholipid, actin and spectrin. Calpactin-I is associated with the cellular plasma membrane as well as the cortical skeleton underlying the plasma membrane and is thought to play a structural role in the cortical skeleton.

Like lipocortin-I, lipocortin-II can act as an inhibitor of phospholipase $A_2$. See Huang et al., supra, and PCT Application Publication No. 86-04094.

Given the similarity of properties and functions of lipocortin-I and lipocortin-II, the isolation of antibodies which are specific to one but not both of the proteins has been a problem which, until the present invention, was not solved. Indeed, at the time of the present invention, it was not apparent that such antibodies could be isolated.

Phospholipase $A_2$ is a key enzyme in providing arachidonic acid for the arachidonic acid cascade, wherein prostaglandins, thromboxanes, and leukotrienes are produced. These compounds have a number of physiological effects, including inflammation.

A number of anti-inflammatory therapeutic agents, such as corticosteroids, are known which act by directly or indirectly, through intermediates induced by the agents, inhibiting phospholipase $A_2$, and, consequently, the production of arachidonic acid and other compounds of the arachidonic acid cascade. Lipocortin-I and lipocortin-II are similarly useful therapeutically as anti-inflammatory agents by virtue of their ability to directly inhibit phospholipase $A_2$. The anti-inflammatory activity of lipocortin-I and lipocortin-II might also be mediated by their blocking the chemotactic movement of neutrophils and macrophages into inflamed tissues. See, e.g., PCT Application Publication No. 86-04094.

Levels of lipocortin-I and lipocortin-II are important in control of inflammation. Thus, the ability to assay for levels of lipocortin-I and lipocortin-II in tissues and body fluids, such as lymph and serum, of a person suffering from a disorder involving inflammation, such as various arthritic, allergic, dermatologic, ophthalmic, and collagen diseases, would provide a useful diagnostic tool for understanding the cause of the patient's disease and selecting therapy appropriate to treat the disease effectively.

SUMMARY OF THE INVENTION

The present invention provides monoclonal antibodies, which are specific for human lipocortin-I or human lipocortin-II but not both proteins, and hybridomas and other types of cells which secrete such antibodies. In particular, three monoclonal antibodies, two of which are specific for lipocortin-II and one of which is specific for lipocortin-I, and the hybridomas for producing the antibodies, have been discovered.

The antibodies of the invention are useful for isolating human lipocortin-II and human lipocortin-I, which, as indicated above, are useful therapeutically, as anti-inflammatory agents. The antibodies of the invention can also be used diagnostically in assaying human tissue and body fluids for levels of lipocortin-I and lipocortin-II.

DETAILED DESCRIPTION OF THE INVENTION

In one aspect, the invention is a culture of a cell, such as an hybridoma, which produces a monoclonal antibody which is specific for one but not both of human lipocortin-I and human lipocortin-II.

Among such hybridoma cultures of the invention, is a culture selected from the group consisting of a culture of hybridoma D1/274.5; a culture of hybridoma B1/107.36; and a culture of hybridoma 74/3.

In another aspect, the invention is a monoclonal antibody which is specific for one but not both human lipocortin-I and human lipocortin-II.

Among such monoclonal antibodies of the invention, is a monoclonal antibody selected from the group consisting of the anti-lipocortin-II antibody produced by a culture of hybridoma D1/274.5; the anti-lipocortin-II antibody produced by a culture of hybridoma B1/107.36; and the anti-lipocortin-I antibody produced by a culture of hybridoma 74/3.

By reference herein to a culture of a specified hybridoma is intended (a) a culture which is the same as a culture of that hybridoma prepared as described in the examples below or a subculture of such a culture, said subculture being on deposit at the American Type Culture Collection (ATCC), as specified further below; (b) a culture of a mutant of such hybridoma, said mutant producing an anti-lipocortin-I or an anti-lipocortin-II antibody, whichever such (non-mutant) hybridoma produces, and said mutant being one which arose spontaneously, during storage, growth or passaging of a culture, or was made deliberately by any process known in the art, including a process of random mutagenesis, as by treatment of a culture with radiation or chemical mutagens or the like, a process of transformation involving transfection or transduction of a culture with nucleic acid by micro-injection, calcium phosphate-mediated uptake of DNA, viral infection or the like, or by a process of cell fusion; (c) a subculture of a culture specified in (a) or (b); or (d) any subculture of a culture specified in (c) regardless of the number of subculturings between the subculture specified in (c) and that specified in this section (d). A culture of an hybridoma also includes a culture grown in vivo, as in the ascites fluid in the peritoneal cavity of a mouse.

The present invention also encompasses cultures of cells, other than hybridomas, which produce monoclonal antibody of the invention. Such cells can be prepared readily by the skilled once a culture of a hybridoma according to the invention, in which a single antibody light chain gene and a single antibody heavy chain gene are transcribed, has been prepared. Hybridomas according to the invention prepared with the Sp2/0 myeloma line (available from commercial sources and from the ATCC under deposit number CRL-1581) or with the FO myeloma line (available from the ATCC under deposit number CRL-1646) are examples of hybridomas in which a single heavy chain gene and a single light chain gene are transcribed. Typically, cultures of non-hybridoma cells according to the invention are prepared as follows:

Using, as the source of mRNA, a culture of an hybridoma according to the invention, in which the only antibody light and heavy chain genes that are transcribed are the light and heavy chain gene corresponding to the monoclonal antibody of the invention made by the hybridoma, full length cDNA is prepared from both the mRNA encoding the light chain and the mRNA encoding the heavy chain of the monoclonal antibody made by the hybridoma. Isolation of these cDNAs is straight-forward, because the two mRNAs are abundant and probes for selecting the mRNAs and cDNAs are readily available based on knowledge in the art of DNA sequences which are common to genes for antibody heavy chains and DNA sequences which are common to genes for antibody light chains. With the cDNAs for the light and heavy chains of the antibody of the invention, expression vectors are readily prepared for transformation of cells to express the light chain or the heavy chain. Both expression vector for the light chain gene and expression vector for the heavy chain gene are co-transfected into cells, in which the vectors are capable of effecting expression of the genes, cells are selected in which both of the genes are expressed, and selected cells are cultured to make a culture according to the invention. Upon expression of the light chain and heavy chain genes in the cells of such a culture, the chains self-assemble into molecules of antibody according to the invention. When made in certain cells, and particularly B-lymphocytes or myeloma cells, the antibody is secreted into the culture medium, as it is from hybridomas, and can be recovered from the medium by standard techniques in essentially the same way that it is recovered from hybridoma culture medium. When made in cells from which antibody is not secreted to the culture medium, antibody is recovered by any of numerous standard techniques from cells that are disrupted to release intracellular protein. Preferred cells for use in preparing non-hybridoma cells according to the invention are mammalian cells. More preferred are B-lymphocytes. Most preferred are myeloma cells, such as Sp2/0 cells, which do not produce antibody or chains thereof.

Reference herein to a culture of a cell, which produces a monoclonal antibody, is intended to include cultures of mutants or derivatives of the cell, which are produced by any means but which produce the monoclonal antibody, as well as subcultures of the culture of the cell, or cultures of mutants or derivatives of the cell which produce the monoclonal antibody, regardless of the number of subculturings between the subculture of interest and the culture of the cell or mutant or derivative thereof. A culture of a cell according to the invention grown in vivo, as in ascites fluid in a mammal's peritoneal cavity, is also a culture of a cell within the present invention.

By reference herein to an antibody which is specific for one but not both of human lipocortin-I and lipocortin-II is meant an antibody which, in any standard test for antibody specificity, such as an Ouchterlony assay or an immunoelectrophoresis assay, binding between the antibody and one but not both of the lipocortins is detected. As a practical matter, in a standard buffer such as PBS at room temperature, an antibody that is specific for one but not both of the lipocortins will have an affinity constant (determined, e.g., by equilibrium dialysis) of greater than about $10^7$ liters/mole for the lipocortin for which it is specific and less than about $10^5$ liters/mole for the lipocortin for which it is not specific.

An hybridoma culture of the invention can be grown by any standard method known in the art. For the preferred cultures of the invention, hybridoma D1/274.5, B1/107.36 or 74/3, standard methods for culturing HAT-resistant, murine hybridomas made with Sp2/0 myeloma cells may be employed.

A monoclonal antibody of the invention is secreted from the cells of the corresponding hybridoma culture of the invention into the culture medium and, also by methods known in the art, can be isolated from the culture medium.

A particularly preferred method of growing an hybridoma culture according to the invention is to inject an aliquot of an hybridoma culture into the peritoneal cavity of a mouse tolerant to the hybridoma cells of the culture, whereupon the cells will grow and proliferate in the ascites fluid. The antibody of the invention then accumulates in the ascites fluid, from which the antibody can be isolated by standard techniques. Mice preferred for this purpose, using the preferred hybridoma cultures of the invention, are Balb/c mice. Older mice are preferred because of their larger size.

A monoclonal antibody of the invention is purified from culture medium or ascites fluid by standard protein purification techniques involving chromatography, such as high performance ®liquid chromatography (HPLC) or fast protein liquid chromatography (FPLC). It is noted that antibody 74/3, unlike antibody D1/274.5 and antibody B1/107.36, does not appear to precipitate efficiently with 50% ammonium sulphate; consequently higher concentrations of ammonium sulfate, or, in place of ammonium sulfate, other salts suitable for salting out immunoglobulins, may be employed in isolating antibody 74/3.

The monoclonal antibodies of the invention are used to isolate human lipocortin-I (antibody 74/3) or human lipocortin-II (antibody D1/274.5 or B1/107.36) by any standard immunoaffinity chromatographic or immunoprecipitation procedure applied to a solution which includes the lipocortin-I or lipocortin-II. Immunoaffinity chromatographic procedures are preferred, because, given the monoclonal antibodies of the invention, which recognize one but not both lipocortin-I and lipocortin-II, such a procedure makes possible the purification of each of these proteins from the other. In this regard, antibody D1/274.5 is preferred over antibody B1/107.36, because, in testing both of these antibodies for reactivity against non-denatured chicken, murine, rat, bovine and human lipocortin-II and denatured human lipocortin-II, the D1/274.5 antibody reacted with only the non-denatured human protein whereas the B1/107.36 antibody reacted with not only the non-denatured human protein but also the rat and bovine proteins. In addition, the B1/107.36 antibody is of IgM subclass and therefore is not as efficient at immunoprecipitation as the D1/274.5 antibody.

The lipocortin-I or lipocortin-II-containing solutions, from which the lipocortin-I or lipocortin-II is isolated employing a monoclonal antibody according to the invention, can be prepared as known in the art from cells, such as various endothelial cells or fibroblasts, which contain the proteins. See, e.g., Huang et al., *Cell*, 46, 191-199 (1986) and Glenney and Tack, *Proc. Natl. Acad. Sci. (USA)*, 82, 7884-7888 (1985). Alternatively, microorganisms, such as bacteria, yeast or mammalian cells, can be genetically engineered to express the lipocortin-I or lipocortin-II and can be cultured under conditions whereby such expression occurs; then a lipocortin-I or lipocortin-II can be obtained by processing the cells or, in case the microorganism is engineered to secrete the expressed protein, the culture medium of the cells. In this regard, see PCT Application Publication No. 86-04094.

The antibodies of the invention can be employed in a known immunological assay to analyze body fluid (e.g., blood serum, lymph) or tissue extracts of a person for the quantity of lipocortin-I (in the case of antibody 74/3) or lipocortin-11 (in the case of antibody D1/274.5 or B1/107.36). However, since the antibodies do not detect denatured protein, they are not suitable for analysis by Western blotting. A determination from such an assay that a person suffering from a disease related to inflammation has an abnormally low level of lipocortin-I or lipocortin-II indicates that a cause of the disease is an abnormally low leVel of the lipocortin. Such a low level is indicative that administration of the lipocortin will ameliorate the inflammation-related disorder.

A culture of hybridoma D1/274.5 has been deposited at the American Type Culture Collection (ATCC; 12301 Parklawn Drive; (Rockville, Md., 20852 U.S.A.) and accorded deposit number HB 9219. A culture of hybridoma B1/107.36 has been deposited at the ATCC and accorded deposit number HB 9220. A culture of hybridoma 74/3 has been deposited at the ATCC and accorded deposit number HB 9218. All of these deposits were made on Oct. 7, 1986, and accepted under the terms of the Budapest Treaty on the Recognition of Deposits of Microorganisms for Purposes of Patent Procedures and the Regulations promulgated thereunder. As such, samples of the cultures will be available to industrial property offices and other persons legally entitled to receive them in accordance with said Treaty and Regulations and in accordance with the patent laws and regulations of every country and international organization in which the present application, or an application claiming priority of the present application, is filed or in which a patent based on such an application is granted.

EXAMPLE I

Preparation of Cultures of Hybridomas D1/274.5 and B1/107.36 Which Produce Monoclonal Antibody Against Human Lipocortin-II Balb/c mice were immunized with either whole live, human AG1523 diploid fibroblasts or crude membrane preparations prepared therefrom. The fibroblasts and membrane preparations are known to include high concentrations of lipocortin-II, as do numerous other fibroblast, endothelial and epithelial cell lines and endothelial and epithelial cells in vivo. The crude membrane preparations were prepared essentially as follows:

AG1523 cells were detached from tissue culture dishes using 2 × Versene (0.6 mM ethylene diaminetetraacetate (EDTA) in 2 x-concentrated phosphate-buffered saline (PBS) free of $Ca^{+2}$ and $Mg^{+2}$), washed 3 times with 1 × PBS and then resuspended at $3 \times 10^7$ cells/ml in 1 × PBS. The cells were subjected to nitrogen cavitation at 800 lb/sq. inch for 5 minutes, the nuclei were removed by centrifugation at 200 × g for 5 minutes and the membranes collected by centrifugation of the supernatants at 25,000 × g for 45 minutes. The membrane pellets were then either frozen in liquid nitrogen for storage or injected directly into the mice.

The immunization schedule of the mice was as follows:

Mice were immunized intraperitoneally with $5 \times 10^6$ AG1523 cells or membranes prepared from $5 \times 10^6$ cells in a final volume of 0.25 ml. Immunizations were performed every 7-10 days on 5 or 6 separate occasions. 3 to 5 days prior to the fusion mice were immunized again intraperitoneally, the animal sacrificed by cervical dislocation and the spleen removed. The spleen was teased apart in 5 ml of HEPES buffer and large debris removed by placing the spleen suspension over 1 ml of fetal calf serum (FCS) for 10 minutes on ice (debris falls to the bottom). The spleen cells and Sp2/0 myeloma cells, which had been selected in 6-thioguanine for 3 days prior, were washed 3 times in Dulbecco-modified Eagle's medium (DME) without serum, and the two sets of cells were counted. Spleen cells and myeloma cells at a ratio of 10:1 were divided into two sets and placed into two 50 ml Falcon tubes, collected by centrifugation and the fusions performed as follows: Polyethylene glycol (PEG) was melted, prepared as a 45% and 25% (v/v) solution with DME and kept at 37° C. To the mixed population cell pellets in the Falcon tubes, the following solutions were added at the specified time:

| Time | |
| --- | --- |
| 0 | 1 ml 45% PEG |
| 1 min | 0.5 ml 25% PEG |
| 2 min | 1 ml DME alone |
| 4 min | 2 ml DME alone |
| 6 min | 4 ml DME alone |
| 8 min | 8 ml DME alone |

During the first 2 minutes the cells were pipetted up and down very gently (with great care) every 30 seconds. With further additions the cells were gently swirled. The cells were then collected by centrifugation and each fusion was added to 100 ml of DME containing HAT and 10% (v/v) FCS. The cells were then plated out into 96-well flat-bottomed tissue culture plates at 200 ul per well. The cells were cultured in the same medium (with HAT) until the hybridomas that arose were screened and then the positive cells were transferred into 24-well Linbro plates. From this stage they were fed with DME containing 10% FCS and HT in place of HAT. Positive hybridomas were then expanded into two 6 cm dishes and frozen down. Meanwhile cloning was performed by single cell dilution into 96-well plates and the cells were continued to be cultured in DME/10% FCS/HT until they were frozen down. After this stage, cells were cultured in DME and 10% FCS alone.

Hybridoma cultures were screened by immunoprecipitation as follows: 75 ul of hybridoma supernatant (or 2×50 ul if testing in pairs), 20 ul of normal mouse serum diluted 1:10 in 0.1% NP40 in PBS and 25 ul of $^{125}$I-iodinated AG1523 cell membranes in lysis buffer (see below) were incubated for 20 min at room temperature in 96-well V-bottomed microtiter plates (Dynatech Labs, Inc., Chantilly Virginia, U.S.A., Cat. No. 1-220-25×9). 70 ul of goat anti-mouse IgG serum was added and the plates incubated overnight at 4° C. The resulting precipitates were washed 4 times with 200 ul of 0.1% NP40 in PBS collecting the precipitates at each stage by centrifuging the plate at 2,000 × g for 30 minutes. The precipitates were then solubilized by heating to 80° C. for 10 minutes with 70 ul of reducing sample buffer (i.e, sample buffer with 2-mercaptoethanol). 25 ul of each sample was loaded onto a 10% polyacrylamide gel and the immunoprecipitates visualized by autoradiography. Antibodies capable of immunoprecipitating an iodinated protein were scored positive.

To $^{125}$I-iodinated membranes, 2×10$^6$ AG1523 cells were detached from tissue culture dishes using 2 × Versene, washed twice in 1 × PBS and resuspended in 1 ml of freshly made glucose:PBS (90 mg per 100 ml). The iodination was started by the ®addition of 100 ul of enzyme mix (50% PBS:45% lactoperoxidase (25 U/ml in PBS):5% glucose oxidase (100 U/ml in PBS) (v/v/v) and 1 mCi of Na$^{125}$I. After 10 min incubation at room temperature the cells were collected by centrifugation, washed twice in PBS, solubilized in 1 ml lysis buffer (0.15 M NaCl, 0.01 M Tris-Cl, 1 mM EDTA, 0.5% NP40, pH 8.2) and the nuclei removed by centrifugation in a microfuge for 5 min. The supernatants containing the iodinated membrane proteins was stored at −20° C. or used immediately. 25 ul of supernatant were routinely used for each immunoprecipitation. Although this procedure is designed for the iodination of cell surface proteins, some of the cells become damaged thus allowing the iodination of intracellular proteins, albeit at a lower efficiency. This accounts for the observation that both lipocortin-I (p35) and lipocortin-II (p36) were iodinated.

Two hybridoma cultures, D1/274 and B1/107, were selected because they produced antibody capable of immunoprecipitating a protein of 36 kDa from AG1523 cells. Cells of these cultures were then subcloned to give stable clones (D1/274.5 and B1/107.36), which, by further analysis, were shown to recognize lipocortin-II (p36). The antibodies were isotyped by a standard procedure, and the D1/274.5 antibody was found to be of IgG$_{2A}$ subclass, while the B1/107.36 antibody was found to be of IgM subclass.

To confirm that the monoclonal antibodies produced by these stable lines were directed against human lipocortin-II, AG1523 cells were cultured with [$^{35}$S] methionine to label newly synthesized proteins, lysed and immunoprecipitated, prepared with either antibody D1/274.5, antibody B1/107.36, a polyclonal anti-chicken anti-lipocortin-II serum known to be broadly species cross-reactive or an anti-chicken lipocortin-II monoclonal antibody, which is known to not cross react with human lipocortin-II, were analyzed by sodium dodecyl sulfate-polyacrylamide gel electrophoresis. Bands were located in the gels with antibodies D1/274.5 and B1/107.36 at the same position as a band for the polyclonal anti-chicken lipocortin-II antibody. No band corresponding to these bands was found in the gel with the anti-chicken lipocortin-II monoclonal antibody. The formal proof that these two antibodies are directed against lipocortin-II (p36) is that the co-migrating $^{35}$S-methionine-labelled bands were excised from the gels, digested with trypsin and the resulting peptides separated in two dimensions on cellulose thin layer plates, by electrophoresis at pH of about 2 in one direction and by chromatography in the perpendicular direction, as described by Hunter and Sefton, *Proc. Natl. Acad. Sci. (USA)*, 77, 1311–1315 (1980). The 36 kDa proteins immunoprecipitated with the D1/274.5 and B1/107.36 antibodies and with the cross-reactive anti-chicken p36 polyclonal antiserum gave rise to identical peptide maps.

The specificity of the monoclonal antibody D1/274.5 for lipocortin-II and its lack of reactivity with lipocortin-I were determined using two-dimensional non-equilibrium-pH gradient gel electrophoresis.

EXAMPLE II

Preparation of Culture of Hybridoma 74/3 Which Produces Monoclonal Antibody Against Human Lipocortin-I Hybridoma 74/3 was isolated in the same way as described in Example I, above, for hybridomas D1/274.5 and B1/b 107.36. It was identified as producing antibody capable of immunoprecipitating a protein of approximately 35 kDa from AG1523 cells. The trypsin-digestion-generated peptide map of $^{35}$S-methionine-labelled protein immunoprecipitated with antibody 74/3 had a pattern clearly distinct from that of the peptide map from trypsin-digestion of $^{35}$S-methionine-labeled lipocortin-II (p36), although one methionine-containing tryptic peptide, which is predicted from comparing the sequences of lipocortin-I and lipocortin-II to be common to the two proteins, was identified in both peptide maps. The trypsin digestion-generated peptide map of $^{35}$S-methionine-labeled lipocortin-1 (p35) was identical to the map generated from a $^{35}$S-methionine-labelled sample of cellular protein immunoprecipitated by antibody 74/3, which, in turn, was identical to the map generated from a sample of $^{35}$S-methionine labelled cellular protein immunoprecipitated by a polyclonal anti-lipocortin-I (p35) antiserum.

The 74/3 antibody was isotyped by a standard procedures and found to be of IgG$_1$ subclass.

EXAMPLE III

Isolation of Antibodies from Hybridomas D1/274.5, B1/107.36 and 74/3 Grown in Vivo To grow a title hybridoma in vivo, Balb/c mice (preferably greater than 5 months of age) were primed with 0.4 ml of 2,6,10,14-tetramethylpentadecane ("Pristane", Aldrich Chemical Co., Milwaukee, Wis., U.S.A., Cat. No. T2,280-2). 7 days later, 1×10$^7$ cells of the hybridoma were injected into the ascites peritoneal cavity in 0.4 ml of culture medium (DME plus 10% FCS). The ascites fluid was removed over the next 6 to 12 days, initially by inserting an 18 gauge syringe needle into the peritoneal cavity and collecting the fluid that was exuded and finally by sacrificing the mice by cervical dislocation and collecting the remaining ascites fluid. The antibody was then isolated from the ascites fluid by a standard technique employing salting out with 50% saturated (NH$_4$)$_2$SO$_4$ (70% in the case of 74/3), followed by FPLC.

The present invention has been described herein with some specificity. Those of skill in the art will recognize variations of, and modifications from, the specifics that are within the spirit of the invention. Such variations and modifications are also within the scope of the invention described and claimed herein.

What is claimed is:

1. A monoclonal antibody that specifically binds one but not both of human lipocortin-I and human lipocortin-II; wherein said antibody is produced by hybridoma D1/274.5, B1/107.36 or 74/3 having ATCC accession numbers HB 9219, HB 9220, and HB 9218, respectively.

2. A monoclonal antibody according to claim 1 which is the anti-lipocortin-II antibody produced by hybridoma B1/274.5 having the ATCC accession number HB 9220.

3. A monoclonal antibody according to claim 1 which is the anti-lipocortin-II antibody produced by hybridoma B1/107.36 have the ATCC accession number HB 9220.

4. A monoclonal antibody according to claim 1 which is the anti-lipocortin-I antibody produced by hybridoma 74/3 having the ATCC accession number HB 9218.

5. A B-lymphocyte transformed to produce a monoclonal antibody that specifically binds one but not both of human lipocortin-I and human lipocortin-II; wherein said antibody is produced by D1/274.5, B1/107.36 or 74/3 having ATTCC accession numbers HB 9219, HB 9220, and HB 9218, respectively.

6. A myeloma cell transformed to produce a monooclonal antibody that specifically binds one but not both of human lipocortin-I and human lipocortin-II wherein said anitbody is that produced by hybridoma D1/274.5, B1/107.36 or 74/3 having ATCC accession number HB 9219, HB 9220, and HB 9218, respectively.

7. A myeloma according to claim 6 wherein, in said transformed myeloma cell, a single antibody light chain gene and a single antibody heavy chain gene are transcribed and said chains are the light chain and heavy chain of the monoclonal antibody produced by hybridoma D1/274.5, B1/107.36 or 74/3 having ATCC accession numbers HB 9219, HB 9220, and HB 9218, respectively.

8. A myeloma according to claim 7 wherein said transformed myeloma cell is a Sp2/0 cell.

9. A hybridoma which produces a monoclonal antibody that specifically binds one but not both of human lipocortin-I and human lipocortin-II, wherein said antibody is produced by hybridoma D1/274.5, B1/107.36 or 74/3 having ATCC accession numbers HB 9219, HB 9220, and HB 9218, respectively.

10. A hybridoma according to claim 9 which is hybridoma D1/274.5 having the ATCC accession number HB 9219.

11. A hybridoma according to claim 9 which is hybridoma B1/107.36 having the ATCC accession number HB 9220.

12. A hybridoma according to claim 9 which is hybridoma 74/3 having the ATCC accession number HB 9218.

* * * * *

UNITED STATES PATENT AND TRADEMARK OFFICE
CERTIFICATE OF CORRECTION

PATENT NO. : 5,051,364   Page 1 of 3
DATED : September 24, 1991
INVENTOR(S) : Isacke, et al.

It is certified that error appears in the above-identified patent and that said Letters Patent is hereby corrected as shown below:

Title Page, item [56]:
    Under "PUBLICATIONS", in the first reference to "Glenney, J.", change "$Ca^{2t}$" to --$Ca^{2+}$--.

Column 1, line 30, change "acting" to --actin--.
    Column 2, line 30, change "Which" to --which--.
    Column 5, line 22, after "performance" delete --®--.
    Column 5, line 56, change "monoclonalantibody" to --monoclonal antibody--.
    Column 6, line 7, change "lipocortin-11" to --lipocortin-II--.
    Column 6, line 14, change "leVel" to --level--.
    Column 6, line 19, before "Rockville" delete "(".
    Column 6, line 44, after "whole" insert --,--.
    Column 7, line 55, change "$^{1251}$I-iodinated" to --$^{125}$I-iodinated--.
    Column 8, line 3, change "$^{1251}$I-iodinated" to --$^{125}$I-iodinated--.

UNITED STATES PATENT AND TRADEMARK OFFICE
CERTIFICATE OF CORRECTION

PATENT NO. : 5,051,364                      Page 2 of 3
DATED     : September 24, 1991
INVENTOR(S) : Isacke, et al.

It is certified that error appears in the above-identified patent and that said Letters Patent is hereby corrected as shown below:

Column 8, line 7, change "th *addition" to --the addition--.

Column 9, line 8, change "B1/b107.36" to --B1/107.36--.

Column 9, line 21, change "lipocortin-1" to --lipocortin-I--.

IN THE CLAIMS: COLUMN 10

Claim 2, line 3, change "B1/274.5" to --D1/274.5--.

Claim 3, line 3, change "have" to --having--.

Claim 5, line 4, after "by" insert --hybridoma--.

Claim 5, line 5, change "ATTCC" to --ATCC--.

Claim 6, lines 1-2, change "monooclonal" to --monoclonal--.

Claim 6, line 4, change "anitbody" to --antibody--.

Claim 6, line 5, change "number" to --numbers--.

UNITED STATES PATENT AND TRADEMARK OFFICE
CERTIFICATE OF CORRECTION

PATENT NO. : 5,051,364
DATED : September 24, 1991
INVENTOR(S) : Isacke, et al.

It is certified that error appears in the above-identified patent and that said Letters Patent is hereby corrected as shown below:

Claim 7, line 5, after "by" insert --said--.

Signed and Sealed this

Twenty-third Day of March, 1993

Attest:

STEPHEN G. KUNIN

*Attesting Officer*  *Acting Commissioner of Patents and Trademarks*